US008166802B2

(12) United States Patent
Fontanili et al.

(10) Patent No.: US 8,166,802 B2
(45) Date of Patent: May 1, 2012

(54) DEVICE FOR DISPLAYING AND MEASURING AIR LOSSES IN A CHEST DRAINAGE APPARATUS

(75) Inventors: Paolo Fontanili, Correggio (IT); Ruggero Paratelli, Ferrara (IT)

(73) Assignee: Eurosets S.r.l., Medolla (IT)

( * ) Notice: Subject to any disclaimer, the term of this patent is extended or adjusted under 35 U.S.C. 154(b) by 239 days.

(21) Appl. No.: 12/309,360

(22) PCT Filed: Nov. 21, 2007

(86) PCT No.: PCT/EP2007/010043
§ 371 (c)(1),
(2), (4) Date: Jan. 15, 2009

(87) PCT Pub. No.: WO2008/064804
PCT Pub. Date: Jun. 5, 2008

(65) Prior Publication Data
US 2009/0266146 A1    Oct. 29, 2009

(30) Foreign Application Priority Data
Nov. 28, 2006   (IT) .............................. MI2006A2291

(51) Int. Cl.
*G01M 3/00* (2006.01)
*A61M 39/22* (2006.01)

(52) U.S. Cl. .......................................... 73/40; 604/246
(58) Field of Classification Search ............ 73/40, 118.2
See application file for complete search history.

(56) References Cited

U.S. PATENT DOCUMENTS

| | | | |
|---|---|---|---|
| 3,363,627 A | 1/1968 | Bidwell et al. | |
| 3,559,647 A | 2/1971 | Bidwell et al. | |
| 4,772,277 A * | 9/1988 | Schiller | 604/321 |
| 6,338,728 B1 * | 1/2002 | Valerio et al. | 604/317 |
| 6,478,774 B1 * | 11/2002 | Balugani et al. | 604/151 |

* cited by examiner

*Primary Examiner* — Hezron E Williams
*Assistant Examiner* — Gregory J Redmann
(74) *Attorney, Agent, or Firm* — Young & Thompson

(57) ABSTRACT

A device for displaying and measuring air losses in a chest drainage apparatus, having a transparent window enclosure with a connection to a tube end connected to a chest cavity to convey exuded liquids for collection a vessel and air losses, a chamber being provided within the apparatus at one of the transparent windows, that contains liquid and comprises the outlet section of a duct for air loss conveying. The device comprises a bell arranged above the outlet section, immersed in liquid at least at a lower end area, and provided, at the submerged portion, with at least one always-open air outflow port and with at least one additional port for the outflow of air.

12 Claims, 5 Drawing Sheets

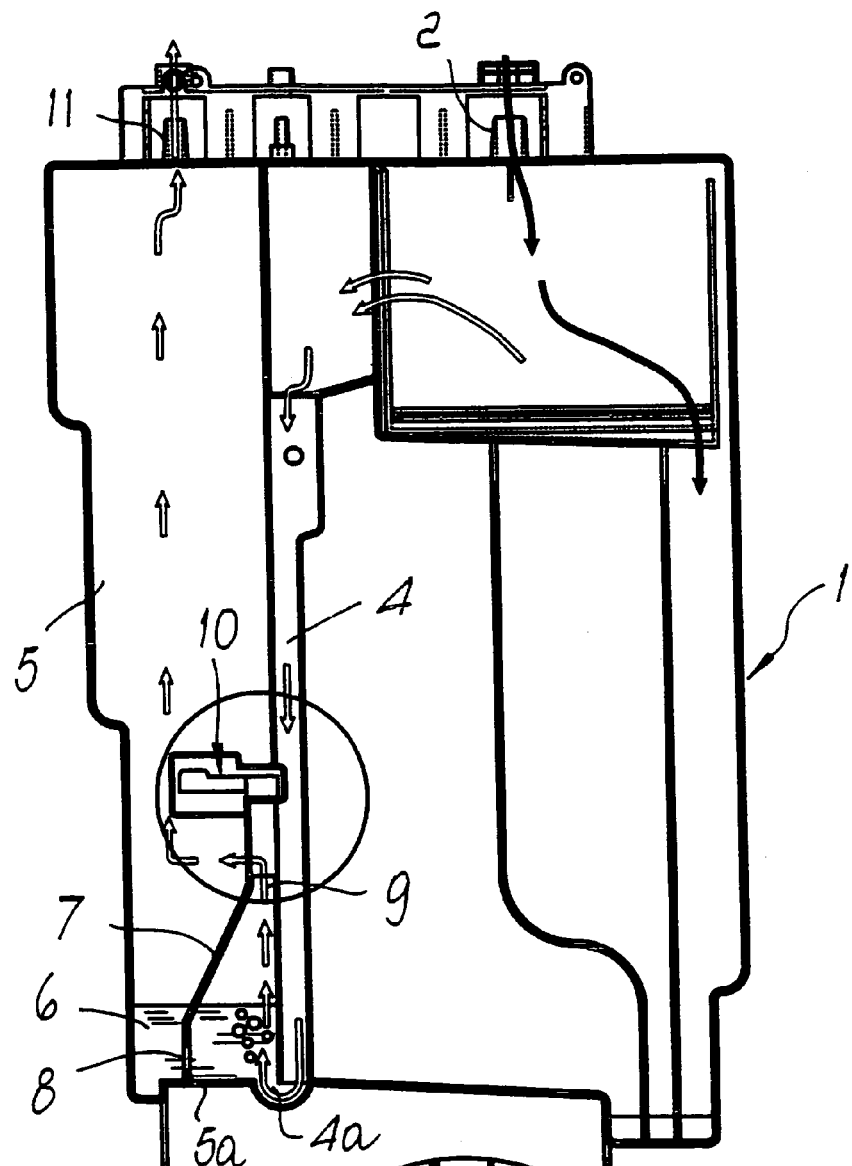
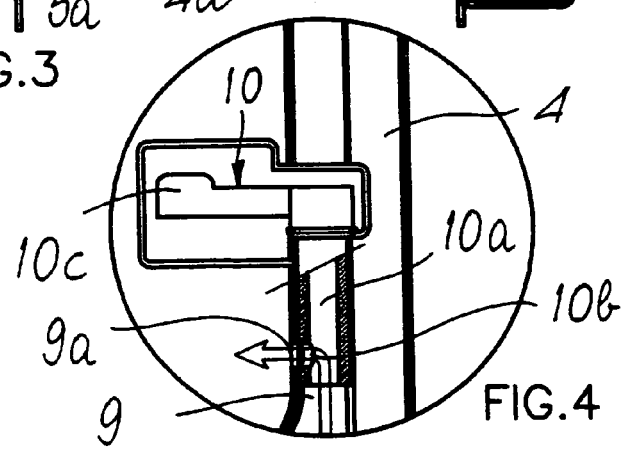
FIG.3
FIG.4

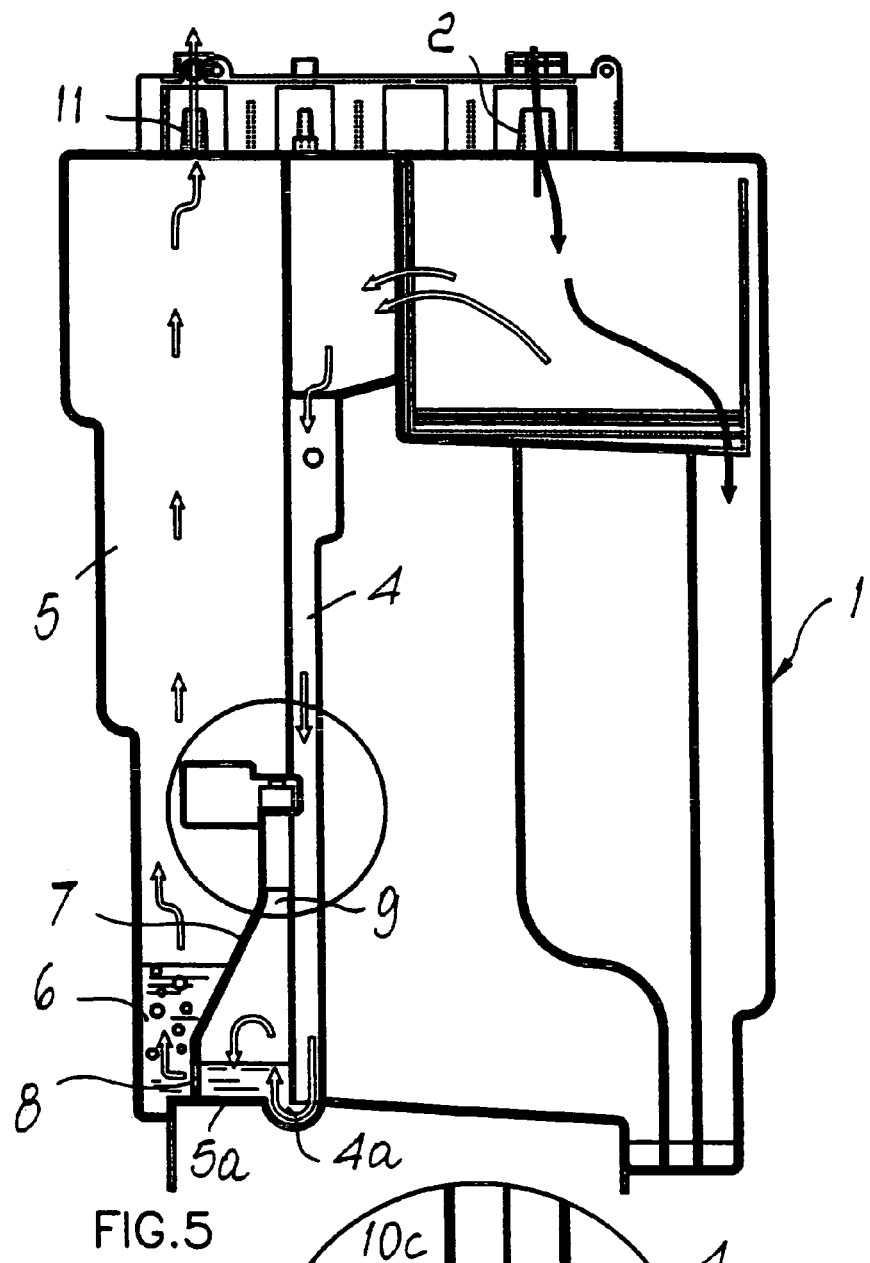
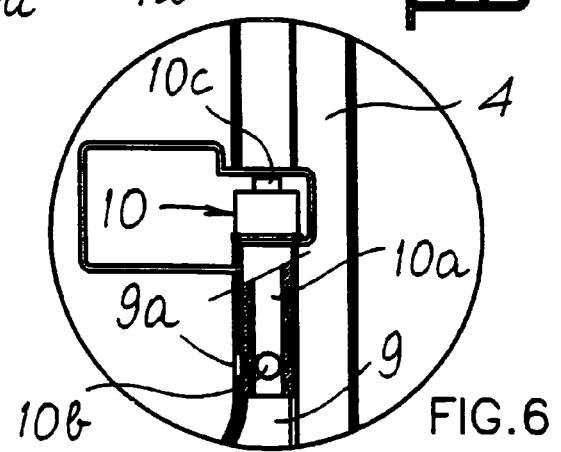
FIG.5
FIG.6

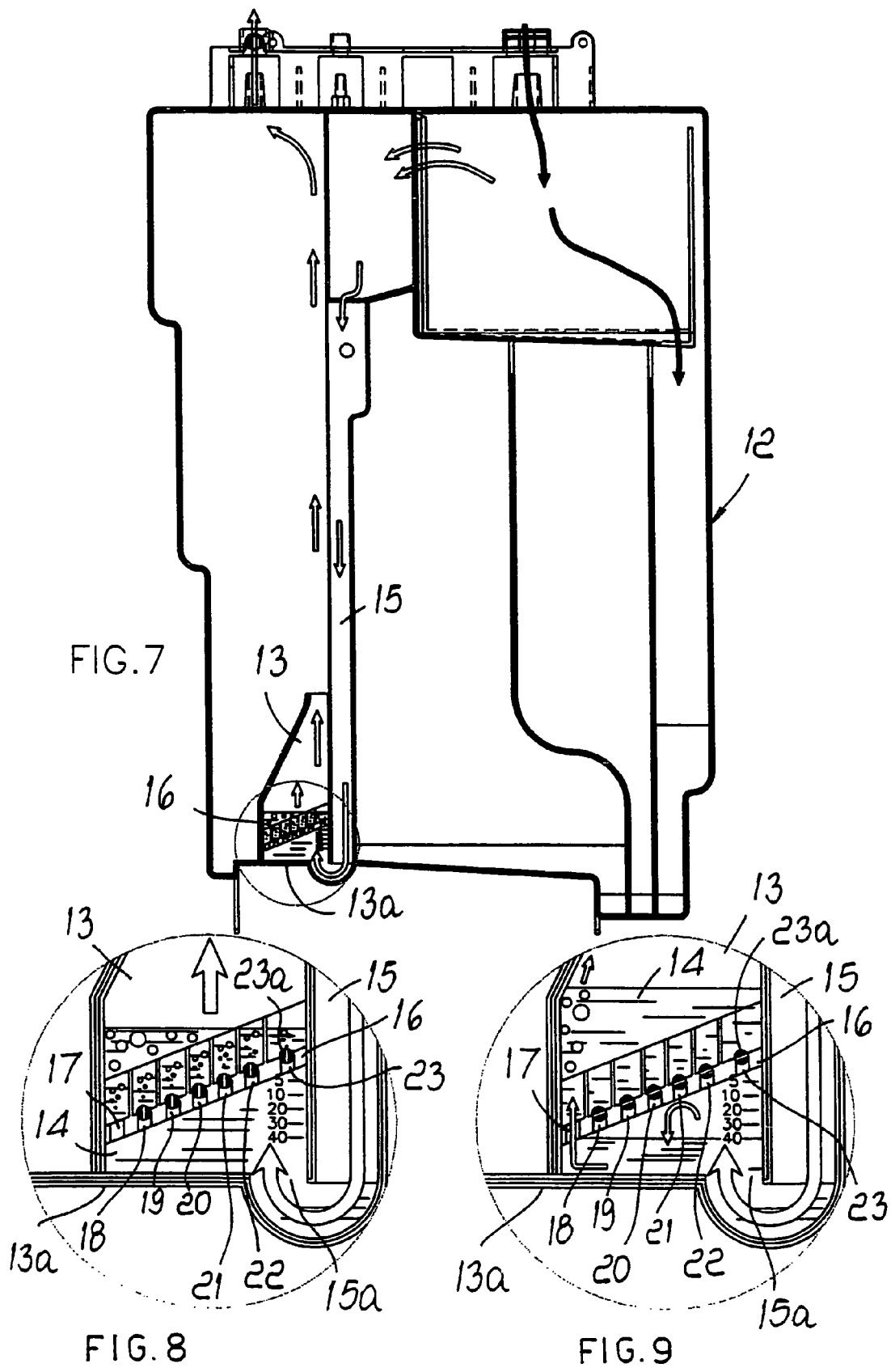

US 8,166,802 B2

DEVICE FOR DISPLAYING AND MEASURING AIR LOSSES IN A CHEST DRAINAGE APPARATUS

The present invention relates to a device for displaying and measuring air losses in a chest drainage apparatus.

BACKGROUND OF THE INVENTION

It is known that chest drainage consists in applying, after surgery or trauma, a tube which is connected to the chest cavity of a patient in order to allow exuded liquids and air losses to be conveyed to an appropriate apparatus.

While the exuded liquids are collected within such apparatus, the air losses, if present, are currently made to pass, before being evacuated from the apparatus, through a device which indeed indicates their presence by utilizing the bubbling of air bubbles within a vessel filled with liquid, usually water or physiological solution.

A device which is particularly widespread in the background art has, for example, a plurality of bubbling ports which are arranged at different distances from where any air losses arrive in the liquid, and this device is capable of providing qualitative information regarding the behavior over time of the extent of such losses by observing the number of ports affected by the phenomenon.

All currently known devices of the physical type provide, as seen for the one mentioned above, simply qualitative and instantaneous indications regarding the presence of any air losses, but today it has become important, as a consequence of research that medicine is conducting in this field, to know precisely the value of the flow-rate of such losses.

SUMMARY OF THE INVENTION

The aim of the present invention is therefore to provide a device of a physical type which, inserted in a chest drainage apparatus, is capable not only of giving a qualitative indication regarding any presence of air losses but also of measuring the flow-rate of such losses.

This aim is achieved by a device for displaying and measuring air losses in a chest drainage apparatus according to the invention, said apparatus being provided with an enclosure with transparent windows which comprises a union for connection to the end of a tube which is designed to be connected, at the other end, to the chest cavity of a patient to convey exuded liquids and air losses, and further comprising a vessel for collecting said liquids, characterized in that it comprises, within said apparatus at one of said transparent windows, a chamber which contains liquid on the bottom and comprises the outlet section of a duct for conveying said air losses, further comprising a bell which is arranged above said outlet section, is immersed in said liquid at least at a lower end area and is provided, at the submerged portion, with at least one always-open port for the outflow of air which is not comprised within the portion of the surface of said bell which lies directly above said outlet section, and with at least one additional port for the outflow of air, which is provided with opening and closure means, said ports for the outflow of the air from the bell being connected to the upper portion of said liquid containment chamber, which is connected to an evacuation union.

BRIEF DESCRIPTION OF THE DRAWINGS

Further characteristics and advantages will become better apparent from the description of two preferred but not exclusive embodiments of the device according to the invention, illustrated by way of non-limiting example in the accompanying drawings, wherein:

FIG. 3 is a sectional view, taken along the line III-III of FIG. 1, in a specific functional situation, as will become better apparent hereinafter;

FIG. 4 is a view of the detail comprised in the circle shown in FIG. 3;

FIG. 5 is a sectional view, as in FIG. 3, but in a different functional situation;

FIG. 6 is a view of the detail comprised in the circle shown in FIG. 5;

FIG. 7 is a sectional view of another embodiment of the device according to the invention;

FIG. 8 is a view of the detail comprised in the circle shown in FIG. 7;

FIG. 9 is a view of the same detail of FIG. 8, but in a different functional situation.

DESCRIPTION OF THE PREFERRED EMBODIMENTS

Figure 1:
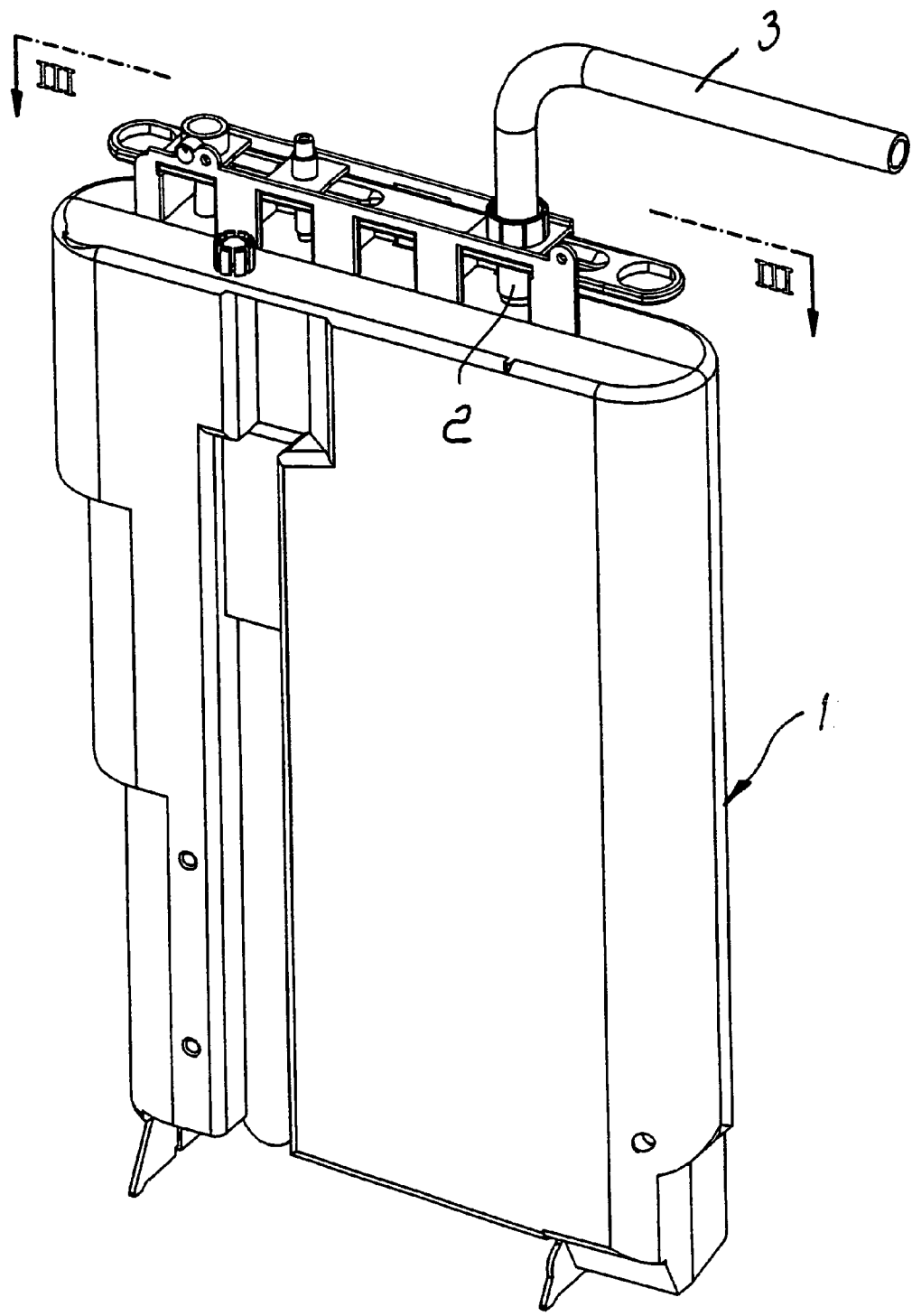
FIG. 1 is a perspective view, taken from the front part, of a chest drainage apparatus which comprises the device according to the invention.

With reference to FIGS. 1 to 6, the reference numeral 1 generally designates a chest drainage apparatus, which is provided with an enclosure with transparent windows, not shown in the figures, and comprises a union 2 for connection to an end of a tube 3 which is designed to be connected, at its other end, to the chest cavity of a patient to convey exuded liquids and air losses.

The black arrows of FIGS. 3 and 5 represent the flow that the exuded liquids follow within the apparatus to reach in a known manner a collection vessel on the bottom of such apparatus.

The flow of the air losses is represented by the white arrows and is conveyed by means of a duct 4 to the device according to the invention.

Such device comprises a chamber 5, which is arranged at one of the transparent windows, which contains liquid 6, very commonly water, on a bottom 5a, and comprises at such bottom an outlet section 4a of the duct 4 which conveys the air losses.

A bell 7 is provided within the chamber 5 in a position which lies above the outlet section 4a and with the lower edge in contact with the bottom 5a.

Figure 2:
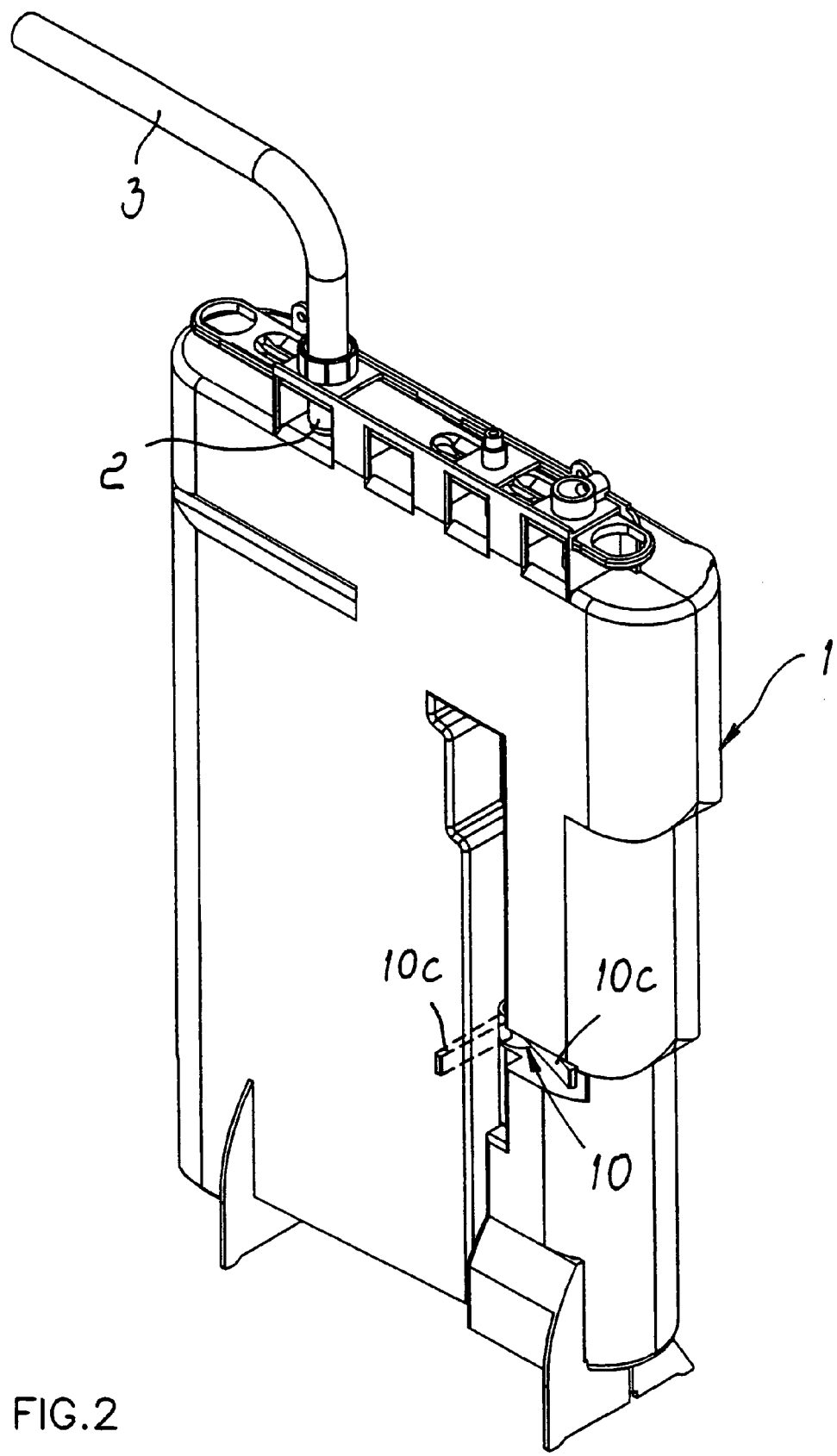
FIG. 2 is a perspective view, taken from the rear part, of the apparatus of FIG. 1.

Such bell, which is immersed in the liquid 6 at the lower area, is provided at such area with a constantly open air outflow port 8, which is arranged distant from the region directly above the outlet section 4a, while in said region there is an air outflow port 9, which is provided with opening and closure means which are constituted by a cock 10, which comprises a hollow cylinder 10a provided with a hole 10b which is adapted to rotate about its own axis between the two positions shown in FIGS. 4 and 6 with the hole 10b respectively arranged and not arranged at a hole 9a provided in the wall of the port 9, by manual actuation on a tab 10c, which in FIG. 2 is shown in a solid line in the position shown in FIGS. 3 and 4 and with dot-and-dash lines in the position of FIGS. 5 and 6.

The air that exits from the bell both by means of the port 8 and by means of the port 9, depending on the functional step that occurs as described hereafter, reaches the upper portion of the chamber 5, which is provided with an evacuation union 11.

Finally, it is noted that the liquid 6 is used at the base of the seal which comprises the duct 4 so as to act as a backflow blocking valve, which is adapted to prevent the inflow of air at atmospheric pressure into the pleural cavity of the patient, in order to avoid the risk of lung collapse.

In the operation of the invention, the port 9 is normally open, and therefore the situation shown in FIGS. 3 and 4 occurs in which the air loss is visualized by the bubbling of the liquid 6 in the bell.

When the physician wishes to pass from a simple visualization of the air loss to the measurement of such loss, he closes the port 9 by operating the cock 10 and thus reaches the situation shown in FIGS. 5 and 6.

The air bubbles, which by their own nature tend to rise, now encounter an obstacle in the wall of the bell 7, thus producing an action on the part of the air for emptying the liquid from the bell through the port 8 until the situation of FIG. 5 is reached.

The time required to empty the bell, which has a known volume, is obviously proportional with an extremely simple ratio and can be tabulated with the flow-rate of the air loss and is timed by the physician, who is thus immediately aware of the measurement of the flow-rate.

Moreover, it should be noted that even during this step, the display of the air loss, shown by the bubbling of the liquid, is not lost.

FIGS. 7, 8, 9 illustrate a device according to another embodiment, which is again comprised within a chest drainage apparatus 12 of the type described previously.

Such device comprises a chamber 13, which contains liquid 14 on a bottom 13a, and comprises, at an end of such bottom, an outflow section 15a of a duct 15 which conveys the air losses.

Within the chamber 13 there is a bell 16, in a position which lies above a section 15a and is totally immersed in the liquid 14; the bell is provided with an air outlet port 17, which is always open and is arranged at the opposite end with respect to the one that lies above the outflow section 15a, and with the plurality of air discharge ports 18, 19, 20, 21, 22, 23, which are distributed substantially uniformly and are provided with corresponding opening and closure cocks 23a for the port 23, with simultaneous manual actuation.

Finally, attention is directed to the presence of a graduation of the level of the liquid contained in the bell in order to offer particular operating modes to users.

Operation of the embodiment now described repeats the conditions described earlier.

With the cocks 23a open, as shown in FIGS. 7 and 8, the air losses are displayed by bubbling in the liquid 14 in the known comparative manner, and therefore massive air losses are matched by bubbling at all the ports 17 to 23, while progressive reduction of such losses is made evident by the progressive reduction of the affected ports, until for extremely small losses it is reduced to bubbling only at the port 23.

By closing simultaneously the cocks 23a, the physician can measure, as shown earlier, the value of the flow-rate of the air losses, deducing it from the time, which can be total or partial by utilizing the level graduation, required to empty the liquid 14 from the bell 16 through the port 17, as shown in FIG. 9.

The described invention is susceptible of numerous other modifications and variations, all of which are within the scope of the appended claims; all the details may further be replaced with other technically equivalent elements.

The disclosures in Italian Patent Application No. MI2006A002291 from which this application claims priority are incorporated herein by reference.

Where technical features mentioned in any claim are followed by reference signs, those reference signs have been included for the sole purpose of increasing the intelligibility of the claims and accordingly, such reference signs do not have any limiting effect on the interpretation of each element identified by way of example by such reference signs.

What is claimed is:

1. A chest drainage apparatus, comprising:
   an enclosure with a transparent window;
   a union for connection to an end of a tube designed to be connected, at another end, to the chest cavity of a patient in order to convey exuded liquids and air losses;
   a collection vessel arranged to receive the exuded liquids from the tube connected to the union;
   a duct (4) arranged to receive and convey the air losses from the tube connected to the union, the duct having an outlet which conveys the air losses; and
   a device for displaying and measuring air losses, the device in communication with the duct, comprising, the device located within the enclosure at the transparent window, the device comprising
   i) a chamber (5) arranged at the transparent window, the chamber holding a liquid (6), the chamber having a bottom (5a) and an outlet section (4a) at the bottom of the chamber, the outlet section connected to the outlet of the duct, the outlet section conveying the air losses to the chamber, the conveyed air losses passing through the liquid into a top portion of the chamber,
   ii) a bell (7) within the chamber, the bell in a position above the outlet section, the bell having a lower edge in contact with the bottom of the chamber, a lower area of the bell immersed in the liquid and containing a volume of the liquid,
   iii) a constantly open air outflow port (8) located in the lower area of the bell immersed in the liquid, the constantly open air outflow port spaced apart from the outlet section of the chamber,
   iv) an air outflow port (9) located above the outlet section of the chamber,
   v) a manually operable, opening and closure element (10) located in the air outflow port,
   the conveyed air losses passing through the air outflow port into the top portion of the chamber when the opening and closure element is in an open position,
   the conveyed air losses not passing through the air outflow port into the top portion of the chamber when the opening and closure element is in a closed position, and
   with the opening and closure element in the closed position the air outflow port is closed causing an action emptying the liquid from the bell through the constantly open air outflow port, a measurement of a flow-rate of the loss of air being determined by a time required to empty the volume of the liquid from the bell.

2. The apparatus according to claim 1, wherein the opening and closure elements each comprise a manually-actuated cock.

3. The apparatus according to claim 1, wherein the liquid within the bell acts as a backflow preventing valve.

4. The apparatus according to claim 1, wherein, when the opening and closure element is in an open position, the air losses are visualized by bubbling in the liquid within the bell.

5. The apparatus according to claim 1, further comprising an evacuation union (11) provided in the upper portion of the chamber.

6. The apparatus according to claim 1, wherein the collection vessel is located at a bottom of the enclosure.

7. A chest drainage apparatus, comprising:
an enclosure with a transparent window;
a union for connection to an end of a tube designed to be connected, at another end, to the chest cavity of a patient in order to convey exuded liquids and air losses;
a collection vessel, located at a bottom of the enclosure and arranged to receive the exuded liquids from the tube connected to the union;
a duct (15) arranged to receive and convey the air losses from the tube connected to the union, the duct having an outlet which conveys the air losses; and
a device for displaying and measuring air losses, the device in communication with the duct, comprising, the device located within the enclosure at the transparent window, the device comprising
i) a chamber (13) arranged at the transparent window, the chamber holding a liquid (14), the chamber having a bottom (13a) and an outlet section (15a) at the bottom of the chamber, the outlet section connected to the outlet of the duct, the outlet section conveying the air losses to the chamber, the conveyed air losses passing through the liquid into a top portion of the chamber,
ii) a bell (16) within the chamber, the bell in a position above the outlet section, the bell having a lower edge in contact with the bottom of the chamber, the bell having a lower part totally immersed in the liquid and containing a volume of the liquid,
iii) a constantly open air outflow port (17) located in the lower part of the bell immersed in the liquid,
iv) a plurality of air discharge ports (18, 19, 20, 21, 22, 23) distributed substantially uniformly within the lower part of the bell and immersed in the liquid,
v) manually actuated, opening and closure elements (23a) located respectively in each of the plural air discharge ports, the plural air discharge ports and opening and closure elements located above the outlet section of the chamber,
with the opening and closure elements in an open position, the air losses are displayed by bubbling in the liquid by a comparative manner, massive air losses being indicated by bubbling at all the air discharge ports, progressive reduction of air losses being indicated by a progressive reduction of the air discharge ports exhibiting bubbling, small air losses indicated by bubbling at only one of the air discharge ports, and
with the opening and closure elements being simultaneously closed, the flow rate of the air losses being determined by a time to empty the liquid from the bell through the constantly open air outflow port.

8. The apparatus according to claim 7, wherein the bell further comprises a graduation of the level of the liquid contained therein, the air discharge ports located along the graduation.

9. The apparatus according to claim 7, wherein the opening and closure elements each comprise a manually-actuated cock.

10. The apparatus according to claim 7, wherein the liquid within the bell acts as a backflow preventing valve.

11. The apparatus according to claim 7, further comprising an evacuation union (11) provided in the upper portion of the chamber.

12. A method for measuring air losses by a chest drainage apparatus, comprising the steps of:
connecting a chest drainage apparatus comprising an enclosure with a transparent window to the chest cavity of a patient in order to convey exuded liquids and air losses from the chest cavity;
collecting the exuded liquids within a vessel of the chest drainage apparatus;
via a duct of the chest drainage apparatus, collecting the air losses within a device for displaying and measuring the air losses located at the transparent window of the chest drainage apparatus,
the device comprising a chamber having a bell located at a bottom of the chamber, the bell containing a volume of liquid, the bottom of the chamber connected to an outlet of the duct so that the air losses bubble through the liquid,
the bell comprising an always-open port for the outflow of the air losses, the always-open port located spaced apart an outlet section of the duct,
the bell further comprising an additional port for the outflow of the air losses, the at least one additional port provided with a manually operable opening and closure element,
the always-open port and the additional port being connected to an upper portion of the chamber, the upper part of the chamber connected to an evacuation union;
closing the opening and closure element to close the additional port for the outflow of air losses to cause an action for emptying the volume of liquid from the bell through the always-open port; and
measuring the flow-rate of the air losses from the time required to empty the volume of the liquid from the bell.

\* \* \* \* \*